United States Patent [19]

Alexander et al.

[11] Patent Number: 5,760,094
[45] Date of Patent: *Jun. 2, 1998

[54] HYDROLYZED GELATIN AS A FLAVOR ENHANCER IN A CHEWABLE TABLET

[75] Inventors: Thomas A. Alexander, Granger; Lawrence J. Daher; Gerald Gold, both of Elkhart, all of Ind.; Clarence L. Hancock, Edwardsburg, Mich.; Donald L. Peterson, Elkhart, Ind.

[73] Assignee: Bayer Corporation, Pittsburgh, Pa.

[*] Notice: The term of this patent shall not extend beyond the expiration date of Pat. No. 5,665,782.

[21] Appl. No.: 851,957

[22] Filed: May 6, 1997

Related U.S. Application Data

[63] Continuation of Ser. No. 434,835, May 4, 1995, Pat. No. 5,665,782, which is a continuation of Ser. No. 283,675, Aug. 1, 1994, abandoned, which is a continuation of Ser. No. 107,202, Aug. 13, 1993, abandoned.

[51] Int. Cl.⁶ .................. A61K 47/42; A61K 9/20; A61K 33/06; A61K 33/08
[52] U.S. Cl. .................. 514/774; 424/465; 424/469; 424/470; 424/682; 424/686; 424/687; 424/688; 424/689; 424/690; 424/691; 424/692; 424/693; 514/960; 514/974
[58] Field of Search .................. 514/774, 960, 514/974; 424/465, 469, 470, 682–693

[56] References Cited

U.S. PATENT DOCUMENTS

| | | |
|---|---|---|
| 3,914,430 | 10/1975 | Cannalonga et al. . |
| 3,947,596 | 3/1976 | Cannalonga et al. . |
| 3,962,384 | 6/1976 | Cannalonga et al. . |
| 4,395,422 | 7/1983 | Schmidt et al. . |
| 4,451,494 | 5/1984 | Roan . |
| 4,771,077 | 9/1988 | Reuter et al. . |
| 4,786,502 | 11/1988 | Chapura et al. . |
| 4,800,087 | 1/1989 | Mehta . |
| 4,831,058 | 5/1989 | Pankhania et al. . |
| 4,835,186 | 5/1989 | Reuter et al. . |
| 4,835,187 | 5/1989 | Reuter . |
| 4,867,986 | 9/1989 | Desai et al. . |
| 4,971,791 | 11/1990 | Tsau et al. . |
| 4,975,281 | 12/1990 | Harwood et al. . |
| 5,013,557 | 5/1991 | Tai . |
| 5,120,761 | 6/1992 | Finnan . |
| 5,147,655 | 9/1992 | Ibsen . |
| 5,178,878 | 1/1993 | Wheling et al. . |
| 5,188,825 | 2/1993 | Iles et al. . |
| 5,223,264 | 6/1993 | Wheling et al. . |
| 5,225,197 | 7/1993 | Bolt et al. . |
| 5,275,822 | 1/1994 | Valentine et al. . |

OTHER PUBLICATIONS

O. Kinnunen and J. Salokannel, "Constipation in Elderly Long–Stay Patients: Its Treatment by Magnesium Hydroxide and Bulk–Laxative," *Annuals of Clinical Research*, 19:321–323, (1987).

Herbert A. Lieberman et al, "Pharmaceutical Dosage Forms: Tablets," Marcel Dekker, Inc., vol. 1, 2nd Ed., pp. 160–163.

Remington Pharmaceutical Science, pp. 1605–1606, Mack Publishing Co., 1985.

*Primary Examiner*—Shep K. Rose
*Attorney, Agent, or Firm*—Burns, Doane, Swecker & Mathis, L.L.P.

[57] ABSTRACT

Hydrolyzed gelatin has been found to provide an improvement in taste and mouthfeel when incorporated in small amounts into chewable tablets containing ingredients requiring taste masking. Medicinals and nutritional supplements may now be prepared as chewables for those who find tablets difficult to swallow, for example children and older adults, or for those who prefer the convenience. There is a particularly large improvement in the taste and mouthfeel of chewables incorporating magaldrate and/or calcium carbonate.

21 Claims, No Drawings

HYDROLYZED GELATIN AS A FLAVOR ENHANCER IN A CHEWABLE TABLET

This application is a continuation of application Ser. No. 08/434,835, filed May 4, 1995, which is a continuation of application Ser. No. 08/283,675, filed Aug. 1, 1994; which is a continuation of application Ser. No. 08/107,202,filed Aug. 13, 1993, both now abandoned.

Chewable tablets are useful for children and for those who have difficulty swallowing tablets. In some cases the normal dosage of medicinal required makes a tablet very large and therefore difficult to swallow. Chewables also have the advantage of portability and easy access and will often provide a rapid delivery system without the use of a liquid dosage form such as a suspension or effervescence. However, one of the problems for chewables which is circumvented by the ordinary swallowable tablet is that the chewing action and residence in the mouth, makes the taste of the medicinal or other ingredients a factor in its acceptability for the consumer. Commonly, some analgesics, antacids and nutritional supplements, for example vitamins, are provided in a chewable form. There has been a recent resurgence of interest in the chewable format and making such a format more palatable. For example U.S. Pat. No. 5,223,264 to Cima Labs Inc. and U.S. Pat. No. 5,225,197 to Beecham Group Plc. disclose chewable tablets containing an effervescent couple which is said to help mask unacceptable flavors and make such tablets more palatable. U.S. Pat. No. 5,178,878, also to Cima Labs, Inc., additionally discloses the use of microparticles containing the pharmaceutical ingredient. After chewing and/or disintegration, the microparticles are swallowed which is said to further enhance the acceptability of the product.

Gelatin has been used previously in tableting primarily as a binder (see Pharmaceutical Dosage Forms: Tablets, Vol. 1, 2ed Edition, Edited by H. A. Lieberman, L. Lachman and J. B. Schwartz). U.S. Pat. No. 5,178,878 mentions the use of gelatin as one of many possible binders. Gelatin has also been used previously as a coating agent or as an encapsulation material for medicinal ingredients which have a particularly noxious taste.

It has now been found, unexpectedly, that small amounts of hydrolyzed gelatin, when incorporated directly into a tablet formulation containing ingredients which are normally considered to be difficult taste masking problems, provides a great improvement in palatability. The hydrolyzed gelatin may be chosen from a number of commercial sources, including POLYPRO® 5000 from G. A. Hormel & Co., Chicago, Ill. and PRIMATONE® G, Scheffield Products Division, Quest International, Norwich, N.Y. POLYPRO, which is a hydrolyzed type B gelatin, is preferred. This gelatin may by added to the ingredients, blended and tableted by standard methods. Encapsulation of the unpalatable ingredients, microencapsulation, or coated layers of unpalatable ingredients are not required. The incorporation of hydrolyzed gelatin additionally improves the palatability of formulations containing effervescent components, such as a fruity acid and a carbonate or bicarbonate source, as are disclosed in the Beecham and Cima patents mentioned previously. However, the addition of effervescent components to mask flavor and provide a palatable tablet is not necessary and the flavor improvement is easily discernable without the effervescent components.

A number of medicinals which require taste masking may be incorporated into chewable tablets in this manner. Such medicinals include, but are not limited to, analgesics such as acetaminophen and non-steroidal antiinflammatories such as aspirin, ibuprofen, ketoprofen and naproxen; expectorants; antihistamines; H2 Blockers such as cimetidine, ranitidine and famotidine; minerals such as calcium, usually in the carbonate form, and iron; and antacids such as magaldrate. (Calcium carbonate is often included in such listings as an antacid itself.) Nutritional supplements often also contain ingredients such as minerals, which require taste masking. It was particularly surprising to find that this simple addition of hydrolyzed gelatin improved the flavor and mouthfeel of chewable tablets containing large amounts of calcium as a supplement and of chewable tablets containing large amounts of the antacid magaldrate. Both of these ingredients are known to be unpleasant to the ordinary consumer. Other medicinals or common ingredients may now be prepared in the chewable tablet format with the inclusion of hydrolyzed gelatin.

The gelatin may be added in small amounts, for example between 2 and 30 mg per tablet, preferably between 2 and 20 mg per tablet, most preferably between 2 and 10 mg per tablet. Surprisingly, a great improvement has been found in the palatability of formulations with a chalky mouthfeel with as little as 3 mg per tablet. Generally, the amount of the gelatin added is so small that it is not necessary to increase the amount of the gelatin simply because of a larger tablet size.

The method of practicing the inventions is further illustrated by the following example.

Example: Chewable Antacid Tablet

A chewable tablet containing magaldrate was prepared from the following formula:

| | |
|---|---|
| magaldrate | 500 mg |
| starch | 120 mg |
| sweetener | 360 mg |
| flavor | 8 mg |
| lubricant | 15 mg |
| hydrolyzed gelatin | 3 mg |

The total tablet weight is approximately 1006 mg. All ingredients were sieved, mixed in a blender and tableted using standard procedures. There were no tableting problems. The taste, when chewed, of the same formulation without the hydrolyzed gelatin was very chalky and unpleasant. In comparison, the taste of this tablet was pleasant and the mouthfeel was greatly improved. A similar formulation may be made with the addition of effervescent components such as a fruity acid (for example citric acid) and a bicarbonate. A similar taste improvement is noted with the further addition of hydrolyzed gelatin.

It should be understood that many modifications and variations can be made in the proportions and components used herein without departing from the spirit and scope of the invention, which is solely defined by the claims.

What is claimed is:

1. A chewable tablet comprising an ingredient requiring taste masking and an effective amount of hydrolyzed gelatin to mask the taste of said ingredient and enhance the flavor of the chewable tablet, wherein said hydrolyzed gelatin is present in an amount of between 2 and 30 mg in said chewable tablet.

2. The chewable tablet of claim 1 wherein the ingredients requiring taste masking are chosen from the group consisting of medicinals and nutritional supplements.

3. The chewable tablet of claim 2 wherein the medicinals requiring taste masking are chosen from the group consisting of antacids, analgesics, $H_2$ blockers, and minerals.

4. The chewable tablet of claim 2 wherein the nutritional supplement includes a mineral component requiring taste masking.

5. A method of making a chewable tablet comprising the steps of:
   a. combining ingredients requiring taste masking, and an effective amount of hydrolyzed gelatin to mask the taste of said ingredient and enhance the flavor of the chewable tablet, wherein said hydrolyzed gelatin is present in an amount of between 2 and 30 mg in said chewable tablet;
   b. blending the combined components; and
   c. tableting.

6. The chewable tablet of claim 1 wherein said gelatin is present in an amount of between 2 and 20 mg per tablet.

7. The chewable tablet of claim 6 wherein said gelatin is present in an amount of between 2 and 10 mg per tablet.

8. The chewable tablet of claim 7 wherein said gelatin is present in an amount of about 3 mg per tablet.

9. The chewable tablet of claim 2 wherein said nutritional supplement is a vitamin.

10. The chewable tablet of claim 2, wherein the medicinal is an expectorant.

11. The chewable tablet of claim 3, wherein the medicinal is an analgesic selected from the group consisting of acetaminophen and non-steroidal anti-inflammatories.

12. The chewable tablet of claim 11, wherein the non-steroidal anti-inflammatory is selected from the group consisting of aspirin, ibuprofen, ketoprofen and naproxen.

13. The chewable tablet of claim 3, wherein the medicinal is an $H_2$ blocker selected from the group consisting of cimetidine, ranitidine and famotidine.

14. The chewable tablet of claim 3, wherein the medicinal requiring taste masking is a mineral selected from the group consisting of calcium and iron.

15. A chewable nutritional supplement tablet which requires taste masking and an effective amount of hydrolyzed gelatin to mask the taste of said chewable tablet and enhance the flavor of said chewable tablet wherein said hydrolyzed gelatin is present in an amount of between 2 and 30 mg in said chewable tablet.

16. The chewable nutritional supplement tablet of claim 15 wherein said gelatin is present in an amount of between 2 and 20 mg per tablet.

17. The chewable antacid tablet of claim 16 wherein said gelatin is present in an amount of between 2 and 10 mg per tablet.

18. The chewable nutritional supplement tablet of claim 17 wherein said gelatin is present in an amount of about 3 mg per tablet.

19. The chewable nutritional supplement tablet of claim 15, wherein said nutritional supplement is a vitamin.

20. The chewable nutritional supplement tablet of claim 15, wherein said tablet comprises a mineral requiring taste masking.

21. The chewable nutritional supplement tablet of claim 20, wherein said mineral is selected from the group consisting of calcium and iron.

* * * * *